(12) United States Patent
Miehle et al.

(10) Patent No.: US 6,247,812 B1
(45) Date of Patent: Jun. 19, 2001

(54) SYSTEM AND METHOD FOR DIAGNOSING AND TREATING A TARGET TISSUE

(75) Inventors: Mark R. Miehle, Del Mar, CA (US); Keith Ignotz, Duluth, GA (US); Ronald Banfiel, Flagstaff, AZ (US); Nathan Morgan, San Diego; Bryan Moore, Carlsbad, both of CA (US)

(73) Assignee: VisMed, San Diego, CA (US)

( * ) Notice: Subject to any disclaimer, the term of this patent is extended or adjusted under 35 U.S.C. 154(b) by 0 days.

(21) Appl. No.: 09/289,608

(22) Filed: Apr. 12, 1999

Related U.S. Application Data

(63) Continuation-in-part of application No. 08/937,375, filed on Sep. 25, 1997, now Pat. No. 5,894,338.

(51) Int. Cl.[7] .......................................... A61B 3/14
(52) U.S. Cl. ................................................. 351/206
(58) Field of Search ..................... 351/200, 203, 351/206, 210, 211, 221; 606/4, 5, 6; 128/203.28; 607/17

(56) References Cited

U.S. PATENT DOCUMENTS 4,790,305 * 12/1988 Zoltan et al. .................. 128/203.28
5,098,426 * 3/1992 Sklar et al. ............................ 606/5
5,720,769 * 2/1998 Van Oort et al. ...................... 607/17

* cited by examiner

Primary Examiner—George Manuel
(74) Attorney, Agent, or Firm—Fleshner & Kim, LLP

(57) ABSTRACT

A device and method for comparing and correlating two or more portions of similar or disparate test data allows a doctor or technician to easily diagnose and/or treat a condition or defect. A device or method embodying the invention can be used for diagnosing vision disorders by correlating visual sensitivity or acuity data to images or data corresponding to biological structures responsible for vision. Such a method allows a doctor to easily identify defects or conditions of a biological structure that causes a loss of vision. In one embodiment of the invention, optical sensitivity data and biological structure data may be stored in multiple data layers, and the data layers can be compared to one another to identify pattern matches between data layers. Similar methods can be used to compare and correlate any two or more types of similar or disparate types of test data. Also, combined presentations of two portions of data can be used to selectively apply treatment to a target tissue. For instance, a previously recorded image can be superimposed on a real-time image to help guide application of a treatment to the target tissue.

46 Claims, 13 Drawing Sheets

RIGHT　　　　　　　　　LEFT

SYSTEM AND METHOD FOR DIAGNOSING AND TREATING A TARGET TISSUE

This application is a CIP of U.S. Ser. No. 08/937,375 filed Sep. 25, 1997 now U.S. Pat. No. 5,894,338.

BACKGROUND OF THE INVENTION

1. Field of the Invention

The invention relates to apparatus and methods for comparing and correlating disparate types of data, or for combining similar types of test data, to provide a combined presentation of the data to aid in the diagnosis and treatment of biological disorders.

2. Background of the Related Art

Frequently, medical doctors and technicians attempt to diagnose a biological disorder of a patient using the results of several different types of tests. This often requires that two or more disparate types of data be correlated and/or compared to one another to determine the cause of a biological disorder or condition. Correlating and/or comparing the disparate types of data can be difficult and time consuming because the disparate types of data are often presented in different formats or in different orientations.

For instance, when a doctor is attempting to determine why a patient has lost some degree of vision sensitivity, he will usually begin by conducting a perimetry test, which determines which areas within a patient's visual field have experienced a loss of sensitivity. The doctor will then attempt to match up a loss of vision sensitivity to a specific eye disorder or biological defect. The eye disorder or biological defect must be determined by examining the biological structures responsible for vision using some sort of testing device. The doctor must then compare and correlate the perimetry data to the data on the biological structures to determine whether a defect or condition of a biological structure is responsible for a measured loss of vision. This comparison is often difficult because of the very different ways that perimetry data and biological structure data are presented, as will be explained below.

Perimetry testing, which measures the sensitivity of a patient's eye, can be done many different ways. The results of a perimetry test are presented on a chart that indicates the sensitivity of one or more eyes at different positions within the eye's visual field. Regardless of the method used, the results are usually presented in one of two different formats.

The results of a perimetry test are shown in a first format in FIG. 1. A plurality of concentric isopter lines 22, 24, 26, 29 are drawn on the chart to indicate the eye's sensitivity. Each isopter line connects points within the patient's visual field having substantially the same sensitivity. The isopter line 22 corresponds to the lowest visual sensitivity, whereas isopter line 29 corresponds to the greatest optical sensitivity. The isopter lines provide a map of how the sensitivity of the patient's vision changes within the field of view.

As can be noted from the chart 20 in FIG. 1, the sensitivity of a person's vision does not vary in a simple proportional manner as one progresses from the center of the line of vision outward towards the fringes of the patient's peripheral vision. In addition, because of the structure of the human eye, a patient's field of vision through an individual eye will always include a blind spot 28 located to the temporal side of the central line of vision. The blind spot 28 corresponds to the point on a person's retina at which the optic nerve is attached.

Perimetry testing is performed on each of a patient's eyes, individually. A chart such as the one shown in FIG. 1 represents the sensitivity of a person's vision through a single eye. However, it is common to present the results of perimetry testing in a chart such as the one shown in FIG. 2, which shows the sensitivity of a person's vision in both the left and the right eyes.

The chart shown in FIG. 2 is arranged such that the left side of the chart corresponds to the patient's vision through his left eye and the right side of the chart corresponds to the patient's vision through his right eye. This orientation is referred to as a "patient's view" orientation. This means that the information corresponding to the left and right eyes are oriented on the page such that they correspond to how a patient would see out into the world.

Perimetry data is presented in a different format in the chart shown in FIG. 3. This chart, which includes a plurality of numbers arranged on perpendicular axes, also indicates a patient's visual sensitivity at different positions within the visual field. The greater the number, the greater the patient's sensitivity at a particular location. The perimetry chart in FIG. 3, like the one in FIG. 2, is arranged in a "patient view" orientation, where the left side represents the visual sensitivity of the patient's left eye and the right side represents the visual sensitivity of the patient's right eye.

As can be seen for the left eye in the chart of FIG. 3, the numerals towards the center of the patient's vision are in the low to mid 30's while the numerals at the edge of the person's vision tend to be in the mid 20's. This indicates that the patient's vision is more sensitive toward the center of his field of vision, and less sensitive toward the edges of his field of view.

Perimetry charts such as the ones shown in FIGS. 2 and 3 indicate the sensitivity of photo-receptors located on the retina of a patient's eye. For a single eye, the sensitivity indicated on the left side of a perimetry chart actually corresponds to photo-receptors located on the right side of the retina. Similarly, the sensitivities indicated on the top of a perimetry chart correspond to photo-receptors located on the bottom of the retina. The inversion of the sensitivity information relative to the location of the photo-receptors is caused by the lens of the eye, which inverts images that pass through the lens. FIG. 4 is a diagram helpful in understanding the inversion of images. The lens 70 of an eye will invert an image 74 as the image is focused on the retina of the eye. The focused image 72 is upside down and is reversed from left to right relative to the original image 74.

A doctor examining a patient's eye will typically look into the patient's eye using a magnifying device to conduct a visual examination of the transparent structures of the eye. To accomplish this examination, light from an instrument is typically beamed into a person's eye, and the light reflects off the structures of the eye, back through the lens 70 of the eye, towards the doctor. Because of the eye's lens 70, the image of the structures leaving the patient's eye is inverted with respect to the location of the actual structures. Some devices that allow a doctor to perform such an examination will simply magnify the image that passes through the lens. Thus, the doctor is viewing an inverted image of the eye structure. Other devices that allow a doctor to conduct such an examination will automatically invert the image that emerged from the lens so that the image of the structures seen by the doctor are correctly oriented relative to the actual structures.

An image of the visible structures of an eye is typically called a fundus image. An example of a fundus image is shown in FIG. 5. A fundus image will usually show the retina of the eye and visible blood vessels. The point at which the optic nerve attaches to the retina usually appears as a lighter area in the image. A portion of the eye called the macula (which corresponds to the center of an eye's field of vision) will usually appear as a darker area in the image.

There are several different types of devices which can record a fundus image of the visible structures of an eye. These devices can record a photographic image of an eye's structure, or they can utilize a charge coupled device to record electronic data corresponding to an image of the eye's structure.

When fundus images of a person's eye are presented, they are typically presented as shown in FIG. 6. The right eye is typically shown on the left hand side of the page, while the left eye is shown on the right hand side of the page. This orientation is called the "doctor view" orientation. Because the devices that obtain fundus images of a person's eye will typically automatically invert the image that passes through the lens of an eye, structures shown at the top of a fundus image correspond to structures actually located at the top of the eye. Similarly, structures appearing on the right hand side of the fundus image correspond to structures actually located on the right side of the eye.

Unfortunately, a doctor may find it difficult to correlate a loss of vision shown in a perimetry chart, such as the ones shown in FIGS. 2 and 3, with the structures shown in a fundus image, such as the one shown in FIG. 6, due to the orientations of the information appearing on a perimetry chart and orientations of the eye structure shown in a fundus image. This difficulty is caused by the presentation of perimetry data in a "patient view" orientation and the presentation of fundus images in a "doctor view" format. The relative positions of the left and right eyes in a fundus image are reversed with respect to the positions of the left and right eyes on a perimetry chart. In addition, due to the inverting effect of the eye's lens, a loss of vision sensitivity indicated at the top portion of a perimetry chart actually corresponds to a loss of sensory ability of the structures located at the bottom of a person's eye. Thus, the information shown in a perimetry chart is actually inverted top-to-bottom and left-to-right with respect to the structures shown in a fundus image. Because the orientation of the data on a perimetry chart is inverted with respect to the structures shown in a fundus image, a doctor can have difficulty relating the information in a perimetry chart to the structures shown in a fundus image. This makes the diagnosis of eye vision disorders difficult and time consuming.

The same types of problems are encountered when other disparate types of test data must be correlated to diagnose a biological disorder or condition.

Similar problems can also occur when a doctor is attempting to actually treat medical conditions or disorders. For instance, if a doctor is attempting to apply some type of treatment to the physical structures of a patient's eye, the doctor must keep in mind the relative orientations of the information shown in perimetry charts and fundus images.

In addition, if a doctor is using some type of real-time imaging mechanism to view a target tissue which is to be treated, it is often necessary for a doctor to apply treatment based on a previously generated or historical image. For instance, if a doctor is attempting to apply some type of light therapy to a biological tissue, such as the retina of an eye, the doctor will typically apply the therapy based on an image of the retina which was previously recorded. Because the doctor cannot simultaneously view both the previously recorded image and the real-time image of the eye, it is often difficult for the doctor to apply the therapy to exactly the right position within the target tissue.

SUMMARY OF THE INVENTION

Embodiments of the invention are designed to provide a combined presentation of data that aids in the diagnosis and/or treatment of a target tissue. A system or method embodying the invention makes it easier and quicker for a doctor or medical technician to diagnose the cause of a biological disorder and/or to treat the disorder using the combined presentation of the data.

Some embodiments of the invention could automatically compare one type of data to at least one other disparate type of data, and combine the data so that the disparate data can be presented together. For instance, in one embodiment of the invention, optical sensitivity data may be combined with data regarding a patient's biological structures responsible for vision. The combined data is presented in a manner that makes it easier for a doctor to diagnose the cause of a loss of vision sensitivity. A device or method embodying the invention may be capable of automatically correlating a loss of vision to a specific biological structural defect or condition to identify the cause of the loss of vision.

In a specific embodiment of the invention, perimetry data taken from a perimetry test is superimposed on a fundus image. It will generally be necessary to invert either the perimetry data or the fundus image to ensure that the sensitivity information reflected in the perimetry data is superimposed onto corresponding structures shown in the fundus image. Also, if data from both eyes is presented in the combined image, the position of the left and right eyes on the page must be reversed in either the perimetry data or the fundus image since the perimetry data appears in a patient view orientation and the fundus images appear in a doctor view orientation.

An example of such a combined image is shown in FIG. 7. The numerals from a perimetry test are superimposed onto a fundus image at the locations of the structures giving rise to the indicated sensitivities. For instance, the perimetry numeral corresponding to the attachment point of the optic nerve 92 is 0, which indicates the patient's blind spot. The numerals surrounding the macula 94 of the eye are greatest, indicating the highest optical sensitivity. The numerals around the exterior edges of the eye are lower, indicating a decreased optical sensitivity. Another example of a combined image of perimetry data (presented in isopter lines) and a fundus image is shown in FIG. 8. In FIG. 8, isopter lines 96 test are superimposed onto a fundus image of a person's eye.

In other embodiments of the invention, any type of optical sensitivity or acuity data may be superimposed onto data reflective of a biological structure responsible for vision. Typically, the structure data will be an image of a portion of a patient's eye. However, structure data for any biological structure responsible for vision could be used. For instance, perimetry data may be superimposed onto an image of a person's optic nerve or a portion of a person's brain responsible for processing vision information, each of which may be obtained through magnetic resonance imaging. Similarly, structure data could be obtained using an infrared test device, an ultrasound test device, a thermal imager, or any other type of test device. Optical sensitivity data could also be superimposed onto an image of the exterior of an eye and its associated eyelid.

In still other embodiments of the invention, individual images of biological structures are stored in separate "structure data layers." Optical sensitivity data is stored in a "sensitivity data layer." Pattern recognition processes are then conducted on each data layer to identify specific patterns in the data. Next, pattern matching between the sensitivity data layer and the structure data layers is conducted to correlate identified patterns in the sensitivity data layer to identified patterns in the structure data layers. This allows large amounts of data to be processed by a computer to rapidly correlate a vision loss to a specific defect or condition of a biological structure that is causing the vision loss.

A device and method embodying the invention, where optical sensitivity data is automatically related to portions of biological structures responsible for vision, make it easy for a doctor to identify specific structural problems and defects that are causing a loss of vision.

In still other embodiments of the invention, any type of test data could be correlated with any other disparate type of test data to create a combined presentation of the test data to make a medical diagnosis easier and quicker. Similarly, a first type of test data could be correlated and compared to multiple different disparate types of test data using a pattern recognition and matching process, such as the one described above.

Other embodiments may combine similar types of data to create a combined presentation. For instance, a system embodying the invention could include means for generating a real-time image of a target tissue, and means for combining a previously recorded image with the real-time image. The previously recorded image could include markers to indicate where the target tissue is to be treated. The combined presentation could then be used by a doctor or other medical personnel to selectively apply treatment to the appropriate regions of the target tissue.

Additional advantages, objects, and features of the invention will be set forth in part, in the description which follows and in part, will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

Embodiments of the present invention will be described in conjunction with the following drawings, wherein like elements are identified with like reference numbers, and wherein.

DETAILED DESCRIPTION OF PREFERRED EMBODIMENTS

Figure 9:
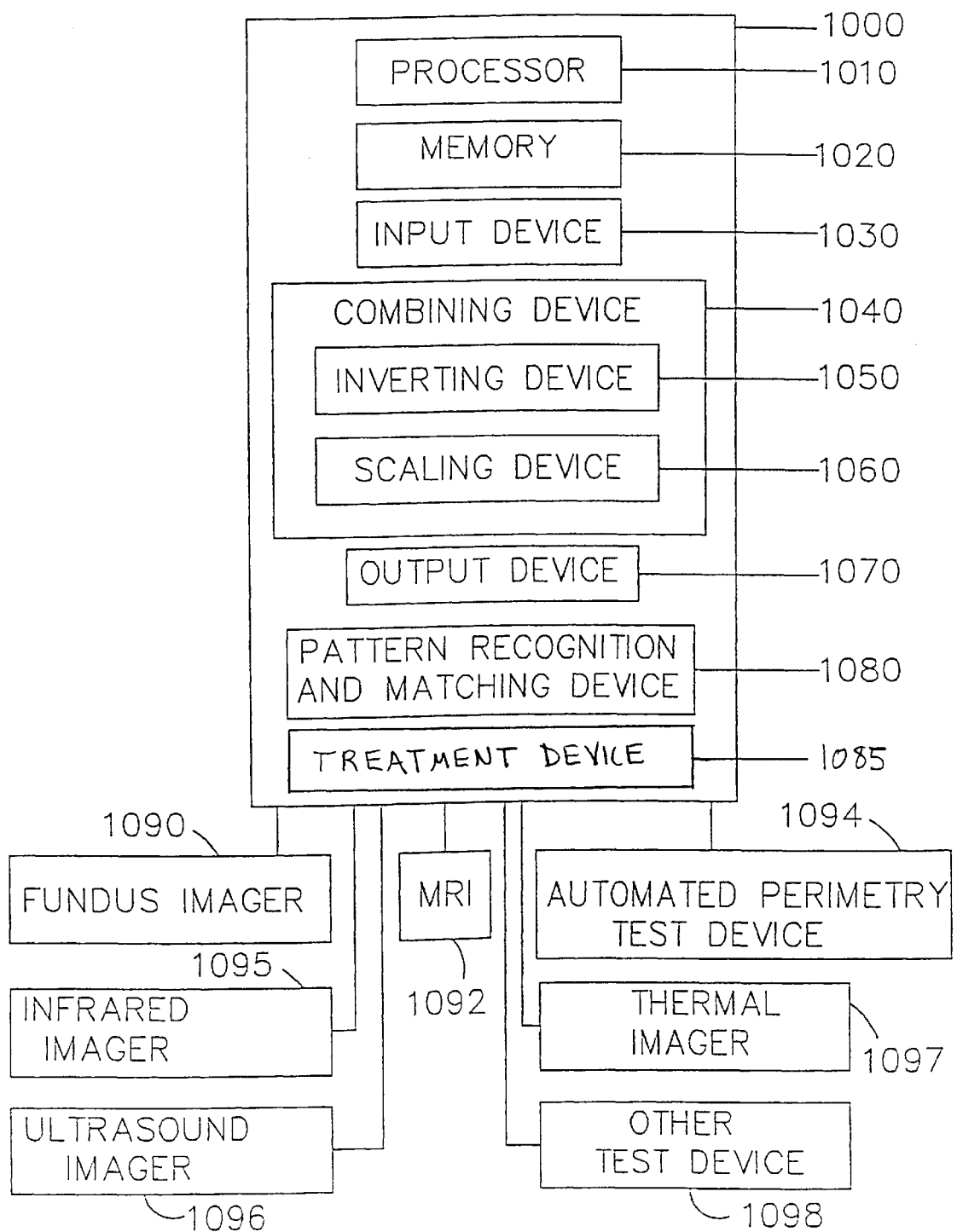
FIG. 9 is a diagram showing the elements of a device embodying the invention.

A diagram of a device embodying the invention is shown in FIG. 9. The device 1000 includes a processor 1010 for processing data, a memory 1020, an input device 1030, a combining device 1040, an output device 1070, a pattern recognition and matching device 1080, and a treatment device 1085. The combining device 1040 includes an inverting device 1050 and a scaling device 1060.

Note, however, many of these individual elements may not be present in a particular embodiment of the present invention. For instance, an embodiment of the invention that is designed to only diagnose a condition of a target tissue may not include the treatment device 1085. Similarly, a device embodying the invention may not include the inverting device 1050 or the scaling device 1060 if the data used by the device does not require inversion or scaling in order to combine the data. As mentioned, other elements shown in FIG. 9 may also not be present in a particular embodiment.

Figure 1:
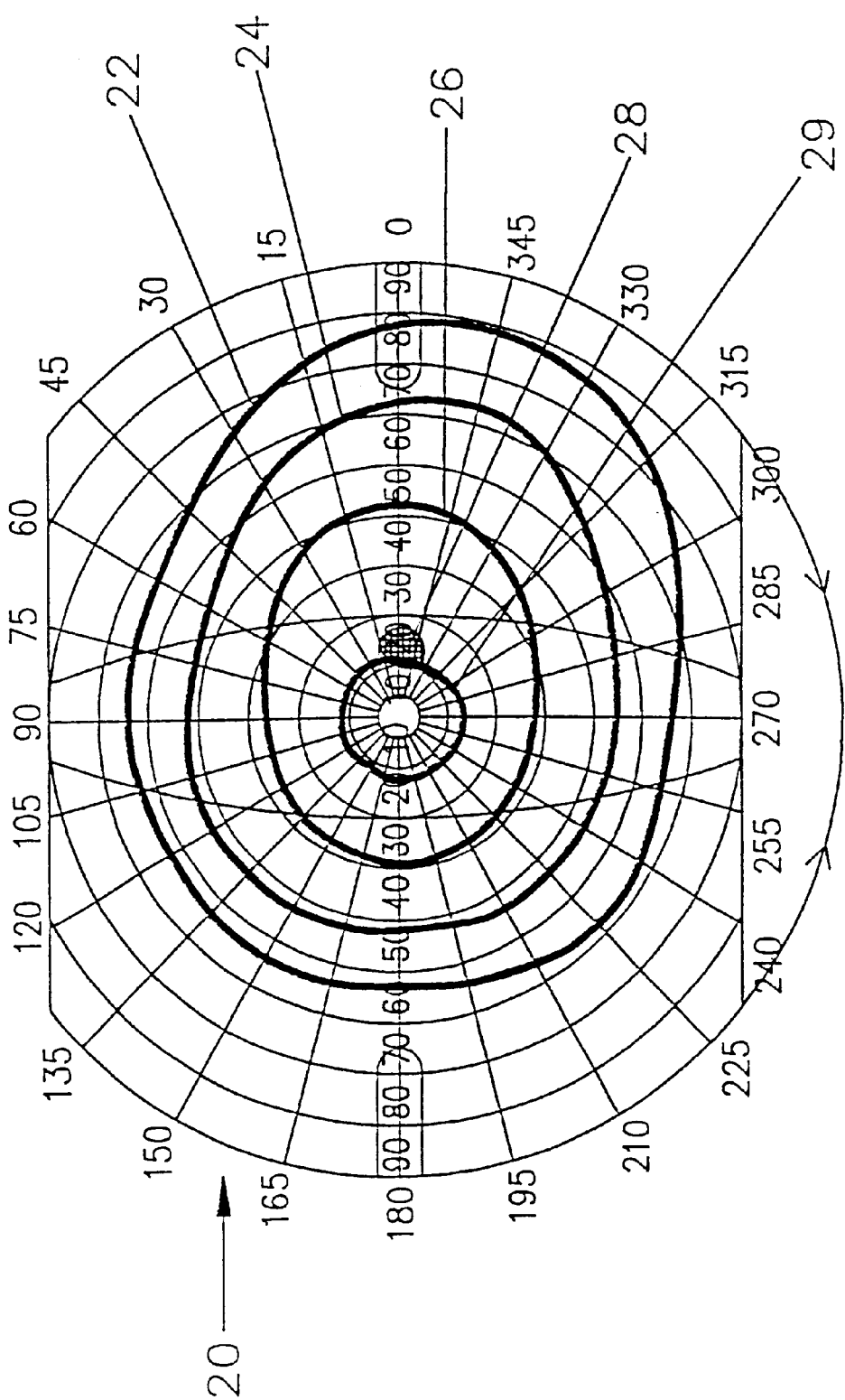
FIG. 1 is a chart showing the results of a perimetry test on a patient's eye.
Figure 2:
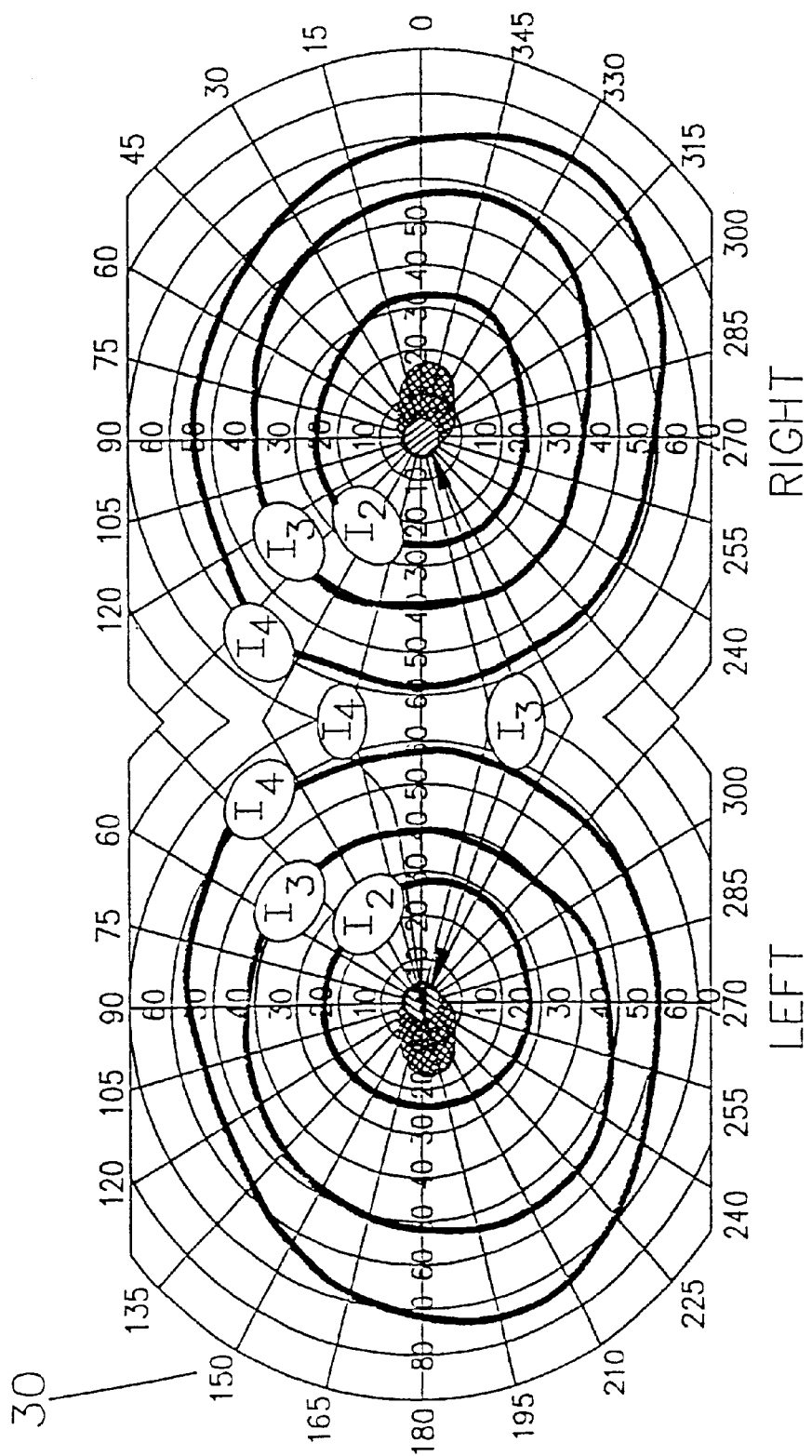
FIG. 2 is a chart showing the results of a perimetry test on a patient's left and right eyes.
Figure 3:
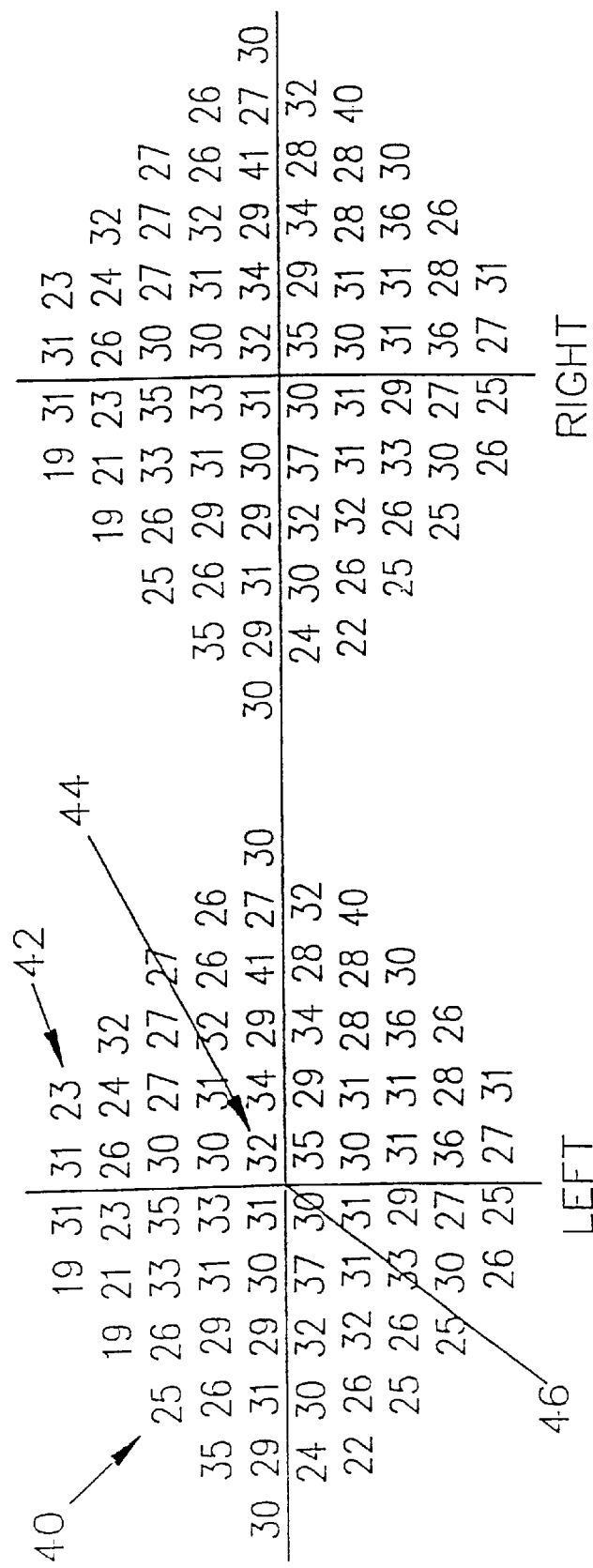
FIG. 3 is a chart showing the results of a perimetry test on a patient's left and right eyes.
Figure 4:
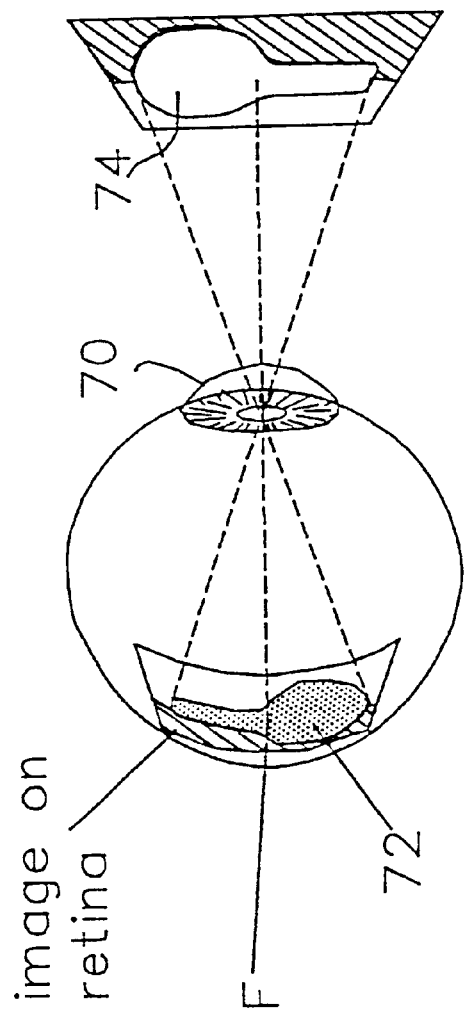
FIG. 4 is a diagram showing how images are inverted when passing through the lens of an eye.
Figure 5:
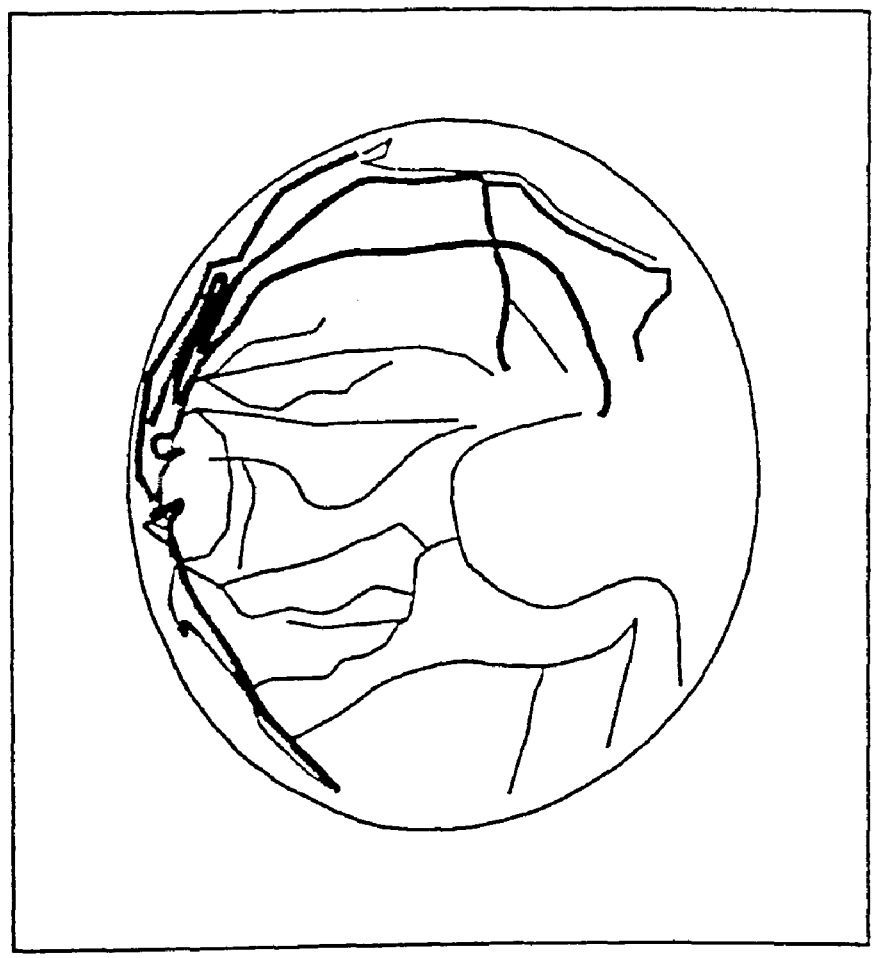
FIG. 5 is a fundus image of an eye.
Figure 6:
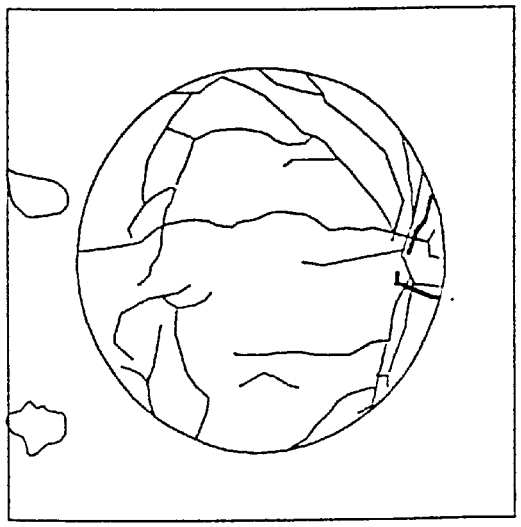
FIG. 6 shows fundus images of a patient's right and left eyes.
Figure 6:
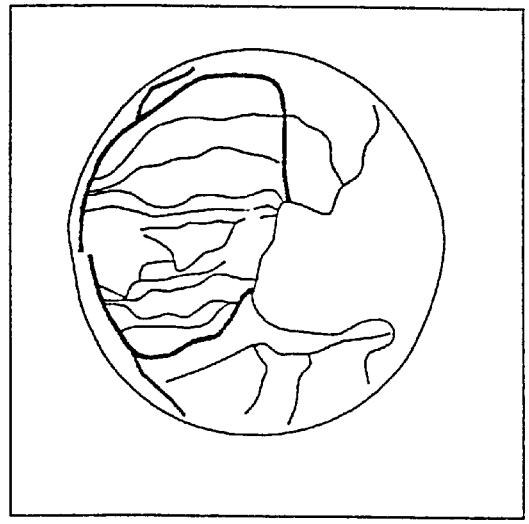

In a first specific embodiment of the invention, optical sensitivity data in the form of perimetry data is correlated to a fundus image of an eye. This involves combining two disparate types of data to create a combined presentation. In the first embodiment, the processor 1010 and the memory 1020 could be part of a typical microcomputer or personal computer. Perimetry data regarding the optical sensitivity of a patient's eye is first input to the device 1000 via an input device 1030. The perimetry data may be in the form of isopter lines or numerals indicative of optical sensitivities. The perimetry data may be input in the form of one or more data files, in which case the input device 1030 could simply be a data input port of a computer, or a magnetic or optical disk reader. Alternatively, the perimetry data could be input by scanning an image of a perimetry chart, such as the ones shown in FIGS. 1, 2 and 3. When a perimetry chart is scanned, the data input device 1030 could comprise a scanner and appropriate software capable of converting a scanned image of a perimetry chart into data that can be used by the processor 1010.

Next, fundus images of the patient's eyes are input to the device 1000 via the input device 1030. The fundus images could be input as one or more data files from a separate fundus imager 1090, or the fundus images could be scanned from images produced by a fundus imager. As noted above, the input device 1030 could comprise a data input port of a computer, a magnetic or optical disk reader, or a scanner and appropriate software for converting a scanned image into data usable by the processor 1010. In yet other embodiments of the invention, the input device 1030 could comprise a device for obtaining an image of a patient's eyes, such as a charge coupled device, and for converting the image into data usable by the processor 1010.

The combining device 1040 then combines the perimetry data and the fundus image data to create a combined image, wherein the perimetry data is superimposed onto the structures in the fundus images giving rise to the indicated optical sensitivities. A user may be able to choose either the patient view or doctor view orientations for the combined image.

Because perimetry data is usually presented in a patient-view format, if a user selects a doctor view orientation for the output, it will usually be necessary to invert the perimetry data with the inverting device 1050 in order for the optical sensitivities represented in the perimetry data to align with the structures shown in the fundus image. Conversely, if a user selects the patient view orientation for the output, it will usually be necessary to invert the fundus image so that the perimetry data can be superimposed on the appropriate structures in the fundus image, and so that the combined image will be in the patient view orientation. Also, if the perimetry data and fundus images are for both eyes of a patient, it will usually be necessary to reverse the orientation of either the perimetry data or the fundus images so that the output is placed in the selected orientation. The inverting device 1050 may comprise a computer program that is run by the processor 1010.

Also, if the scale of the perimetry data does not match the scale of the fundus image, it will be necessary to scale either the perimetry data or the fundus image so that their sizes match and the perimetry data may be superimposed on the appropriate structures shown in the fundus image. Scaling the perimetry data to match the fundus image can be accomplished using the scaling device 1060 of the combining device 1040. The scaling device 1060 may also comprise software that is run by the processor 1010.

In one embodiment of the invention, the scaling device 1060 selects reference points in both the perimetry data and the fundus image, and either the perimetry data or the fundus image are enlarged or reduced until the reference points coincide. For instance, in the fundus image, the location of the attachment point of the optic nerve can be identified as a lighter portion of the image, and the location of the macula can be identified as a relatively dark area within the fundus image. In the perimetry data, these two locations correspond, respectively, to the blind spot where optical sensitivity is zero, and the central portion of the field of vision where optical sensitivity is highest. The scaling device 1060 may be a computer program run by the processor 1010 that identifies these reference points in the perimetry data and the fundus image, and then alters the scale of either or both the fundus image and the perimetry data until the reference points coincide in a combined image.

Figure 7:
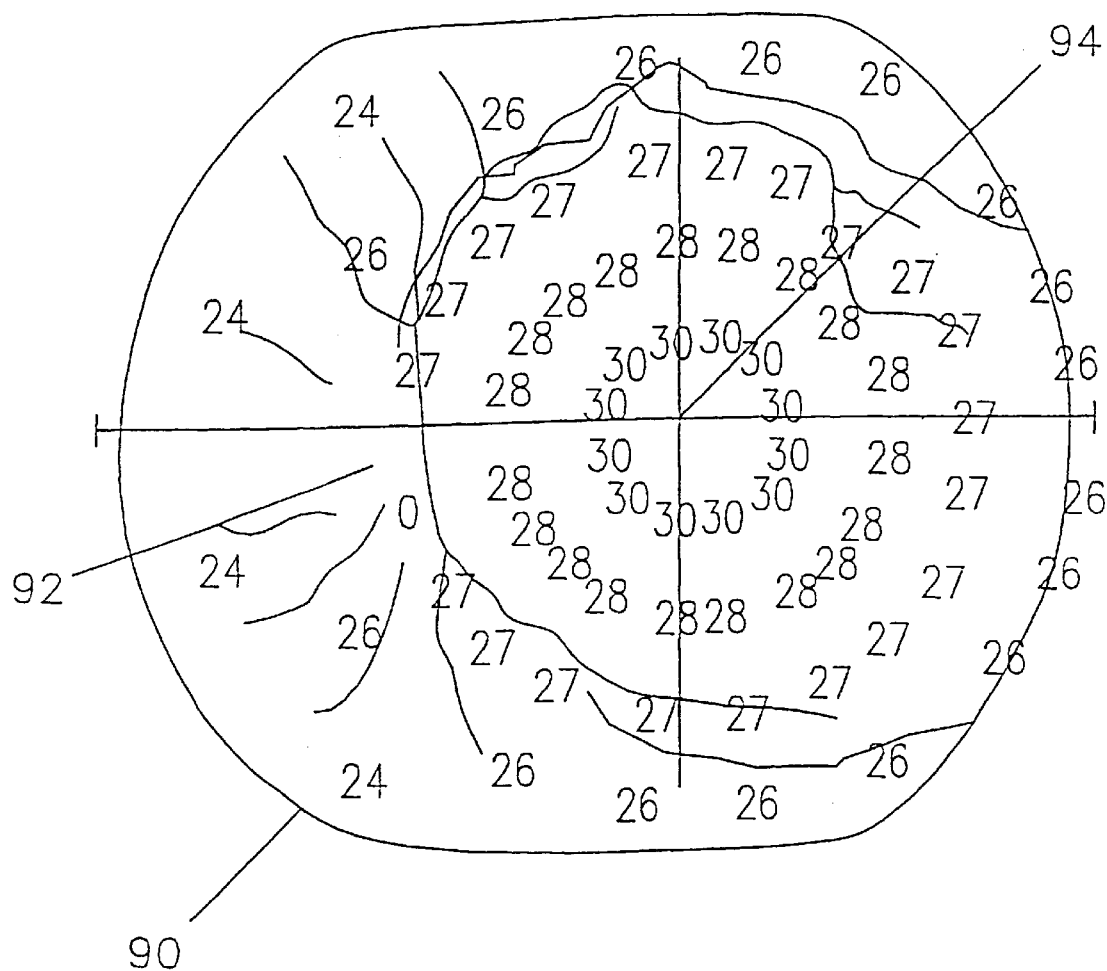
FIG. 7 is a combined image of perimetry data and the fundus of an eye.
Figure 8:
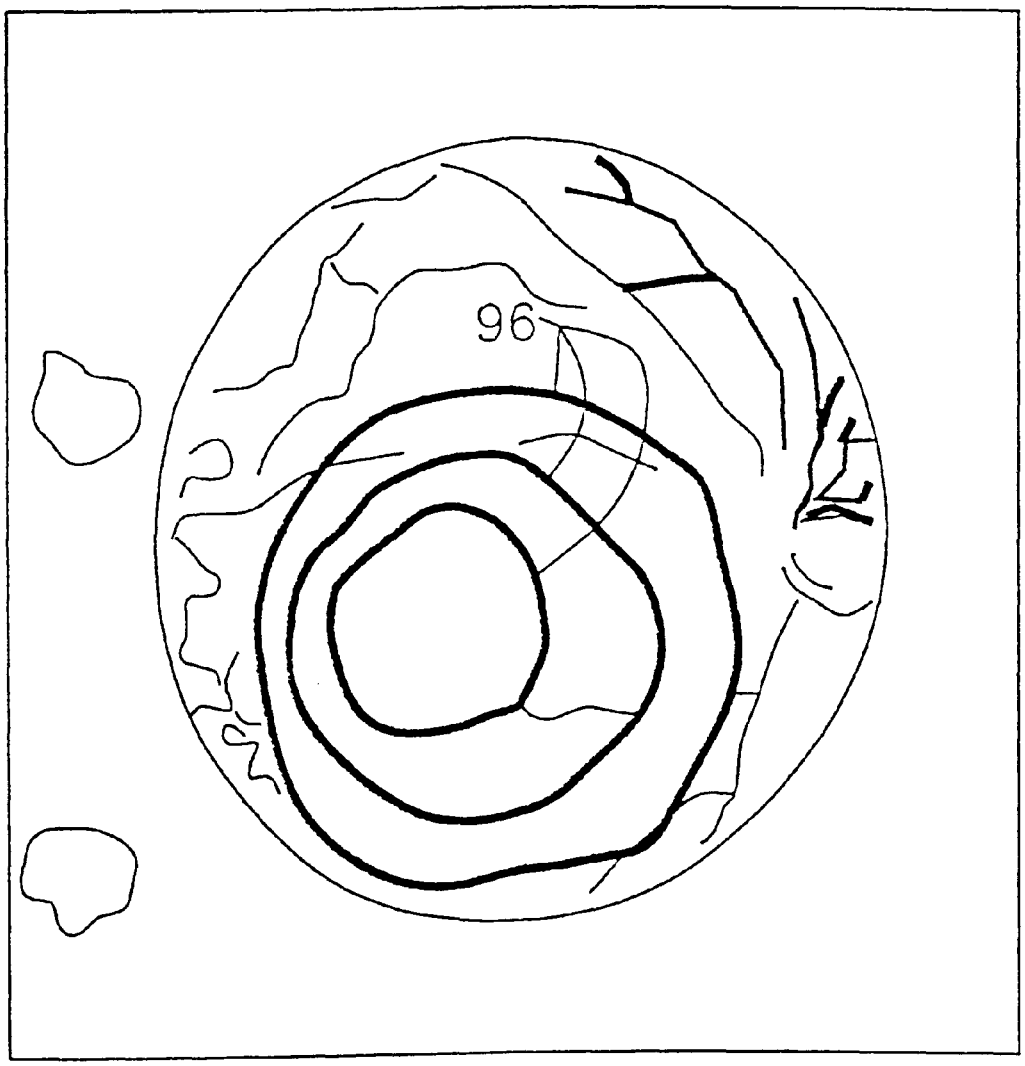
FIG. 8 is a combined image of perimetry data and the fundus of an eye.

After the combining device creates a combined image of the perimetry data and the fundus image, the output device 1070 outputs the combined image, which can then be examined by a doctor to aid in the diagnosis of vision defects. Examples of a combined image of perimetry data and a fundus image are shown in FIGS. 7 and 8. Although FIGS. 7 and 8 show a combined image for only a single eye, the device 1000 could create combined images for both the left and right eyes of a patient, and the combined images could be presented in a single printout in either the patient view or doctor view formats.

The output device 1070 could comprise a computer screen upon which the combined image is displayed, a printer that prints the combined image, a photographic device that creates a negative or photographic print of the combined image, or a projector that displays the combined image on a large screen. Alternatively, the output device 1070 could comprise any other device capable of displaying the combined image to a user. For instance, should three dimensional holographic projectors become available in the future, such a device would be ideal for presenting a user with a combined three dimensional image of the perimetry data and fundus image.

Other embodiments of the invention could combine perimetry data with images of other structures of a patient responsible for vision. For instance, a device embodying the invention might combine perimetry data with an image of an optic nerve or an image of a portion of a patient's brain responsible for vision taken through magnetic resonance imaging (MRI) or other means. In an embodiment using an image of an optic nerve, the combining device 1040 would manipulate the input optic nerve image data and/or the perimetry data such that the perimetry data is superimposed on corresponding portions of the optic nerve image.

In yet another embodiment of the invention, the optical structure data may comprise an image of the exterior of an eye and its associated eyelid. Some medical conditions cause the eyelid of a person's eye to droop over the eye, thus obscuring a portion of the person's field of vision. By combining an image of an exterior of an eye and the associated eyelid with perimetry data from a perimetry test, one can determine whether the drooping of the eyelid gives rise to a measurable loss of vision.

Other embodiments of the invention could create combined images showing perimetry data superimposed onto an image of any other biological structure responsible for vision. Also, although the figures show the perimetry data represented as numerals or isopter lines, the perimetry data could also be represented by any type of user recognizable symbol or pattern that is indicative of the sensitivity of the patient's eye.

In yet other embodiments of the invention, images of biological structures responsible for vision could be combined with optical sensitivity or acuity data other than perimetry data. Any type of optical sensitivity or acuity data could be correlated to biological structures by a device or method embodying the invention to aid a doctor in diagnosing vision disorders.

In still other embodiments, data indicative of a biological structure responsible for vision, other than image data, may be correlated to optical sensitivity data. Although image data is described for many of the embodiments, any type of structure data could be used. For instance, images or structure data may be obtained by an ultrasound imager 1096, an infrared imager 1095, a thermal imager 1097, another type of electromagnetic radiation testing device, or any other type of test device 1098.

In addition, the principles of the invention are not limited to correlating optical sensitivity data to biological structure data. A device or method embodying the invention could be used to combine any two or more disparate types of data obtained through any testing devices. As mentioned above, it is quite common for a doctor or medical technician to correlate the results of disparate tests in attempting to diagnose a biological disorder or condition. A device embodying the invention and incorporating a pattern recognition and matching device could be used to correlate the results or any disparate tests, as will be explained below.

A device embodying the invention and including a pattern recognition and matching device 1080 could be used to correlate vision sensitivity or acuity data, such as perimetry data, with data regarding a biological structure responsible for vision. For instance, in an embodiment of the invention employing a pattern recognition and matching device 1080, perimetry data could be compared to multiple images of a patient's brain responsible for processing vision information. Each of the plurality of images of the patient's brain, which could be separate scanned slices of the brain taken with a magnetic resonance imager or other image generating device, would be stored in a separate "structure data layer." Each structure data layer could comprise a digital data file corresponding to an image of the brain. The perimetry data could also be stored in a "perimetry data layer," which could also comprise a digital data file corresponding to a perimetry data chart.

Once the structure data layers and the perimetry data layer have been created, the device 1000 would carry out a pattern recognition process utilizing the pattern recognition and matching device 1080. In the pattern recognition process, each of the data layers would be examined in turn, in an attempt to identify patterns appearing in the data. Once patterns have been identified in each of the data layers, the pattern recognition and matching device 1080 would attempt to match up identified patterns in the perimetry data layer with corresponding patterns appearing in one or more of the structure data layers. The device could thus rapidly identify a correlation between a loss of vision, as reflected in the perimetry data, and a structural defect or condition that can be discerned in the magnetic resonance images of the brain.

A similar pattern recognition process could be carried out with structural data regarding any portion of a biological structure of a patient responsible for processing vision, such as an optic nerve, or structures within a person's eye. Also, such a pattern recognition process could be conducted with any type of visual sensitivity or acuity data, not just perimetry data. Further, the pattern recognition and matching device could be used to compare and correlate any two or more disparate types of data to aid a doctor in arriving at a diagnosis. This process is not limited to vision disorders.

As shown in FIG. 9, a device 1000 embodying the invention may be directly connected to a fundus imager 1090, a magnetic resonance imager 1092, an automated perimetry test device 1094, an infrared imager 1095, an ultrasound imager 1096, a thermal imager 1097 or any other type of test device 1098 so that information can be easily exchanged between the devices. When the device 1000 is connected to one or more of these elements, the device would be capable of automatically testing a patient and correlating the test data in an attempt to determine the cause of a biological defect or condition.

Figure 10:
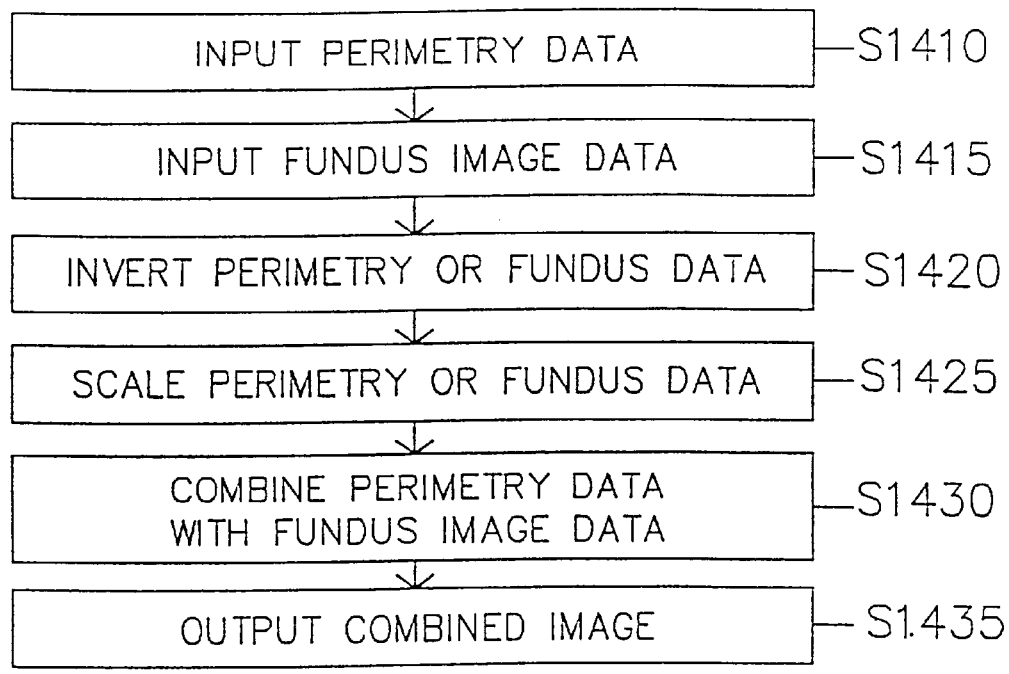
FIG. 10 is a flow chart showing the steps of a method embodying the invention.

A method embodying the invention is shown in FIG. 10. In this method, perimetry data and fundus image data are input to a device and the device creates a combined image where the perimetry data is superimposed on the fundus image. Although this example is related to comparing and correlating vision information, a similar process could be used to correlate any two disparate types of data to create a combined presentation of the data that would aid a doctor in arriving at a diagnosis.

In a first step 1410, perimetry data is input to a device. The perimetry data could be input in the form of one or more data files, or perimetry charts could be scanned. In step 1415, a fundus image is input. The fundus image could also be input as a data file, or a fundus image could be scanned. In yet another embodiment, data from a charge coupled device focused on an eye could be directly input in either an analog or digital form. The fundus image could also be input using any other sort of data input device or scanner capable of inputting data representative of the fundus image.

In step 1420, either the perimetry data or the fundus image are inverted. Typically, a user would select either the doctor view or patient view orientation for the combined presentation. If the patient view orientation is selected, the fundus image (which is usually in the doctor view orientation) would be inverted. If the doctor view orientation is selected, the perimetry data (which is in the patient view orientation) would be inverted.

In step 1425, either the perimetry data or the fundus image, or both, are scaled so that the perimetry data can be superimposed on the fundus image such that the perimetry data overlies corresponding structures in the fundus image. The scaling step could be performed as described above, wherein two reference points are determined on both the perimetry data and the fundus image, and the scale of either or both of the perimetry data and the fundus image is altered until the reference points coincide.

In step 1430, the perimetry data is combined with the fundus image data to create a combined image. Finally, in step 1435, the combined image is output. The combined image may be output using a printer, a plotter, or the combined image may be displayed on a computer or projection screen. Any type of output device capable of creating or displaying the combined image could be used to perform the output step.

A method embodying the invention and similar to the one described above could also be used to create combined images of any type of optical sensitivity or acuity data with structural data regarding any biological structure responsible for vision. For instance, visual sensitivity data could be combined with an image of the exterior of an eye and its associated eyelid, an image of an optic nerve, or an image of a portion of a brain responsible for processing vision information. In addition, such a method could be used to combine and correlate any two disparate types of data to create a combined presentation of data, the data need not relate to vision. Also, the output step might further comprise altering the combined image to present the combined image in a patient view or a doctor view format.

Figure 11:
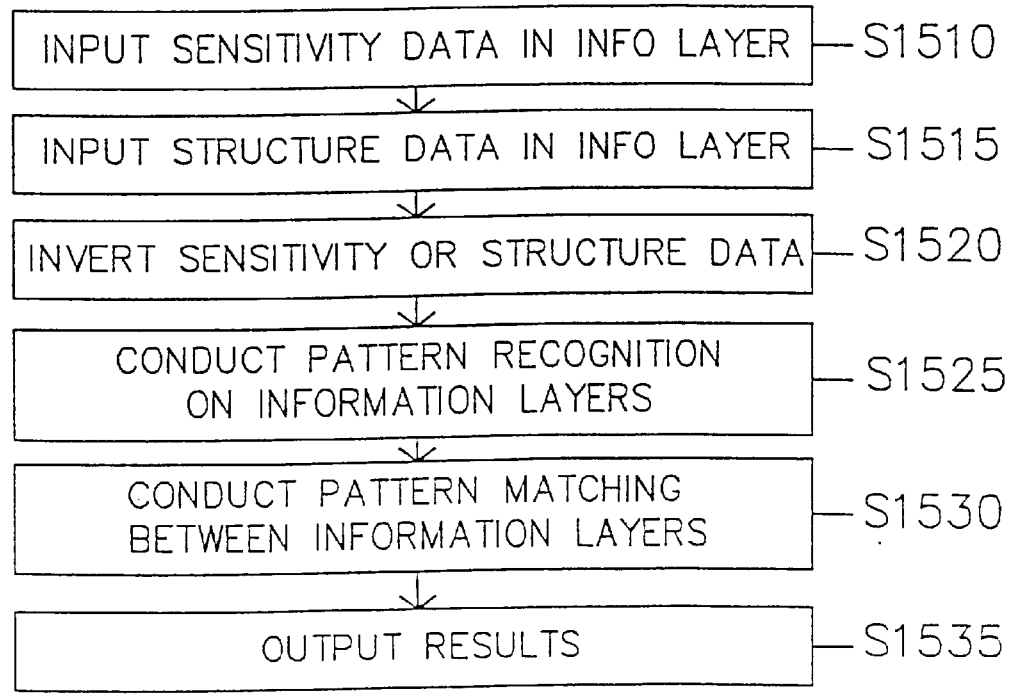
FIG. 11 is another flow chart showing the steps of another method embodying the invention.

Another method embodying the invention is shown in FIG. 11. In this method, optical sensitivity data and optical structure data are stored in data layers, and a pattern matching process is performed to identify defects or conditions of a patient's biological structures that correlate to a loss of vision sensitivity, as reflected in the sensitivity data. Although this process is described in conjunction with optical sensitivity and structure data, any two types of disparate data could be compared to one another using this method in an attempt to correlate patterns in the data.

In a first step 1510, vision sensitivity data, such as perimetry data, is input to a sensitivity data layer. The vision sensitivity data may be input in the form of data files, or it may be scanned from a perimetry chart. In step 1515, structural data is input into at least one structure information data layer. If multiple images of a biological structure responsible for vision are obtained, each of the images may be stored in a different structure information data layer.

In step 1520, either the sensitivity data layer or the structure data layer is inverted so that the orientations of each of the data layers is the same. This step may not be necessary if the input data is already in the same orientation. Also, if a user selects an output orientation for the data, this may determine which of the data layers is inverted, as described above in connection with the method shown in FIG. 10.

In step 1525, a pattern recognition process is performed to identify one or more patterns in each of the data layers. In step 1530, any patterns identified in the sensitivity data layer are compared to patterns identified in the structure data layers. An attempt is made to match the identified patterns to correlate a defect or condition of the biological structure with a variation of vision sensitivity, as noted in the sensitivity data. In step 1535, the results of the pattern matching step are output. The results may be output in the form of a report, or in the form of a combined presentation of the two types of data. For instance, a combined image which superimposes perimetry data on at least one image of a biological structure may be output.

Although the method described above utilizes vision sensitivity data and biological structure data, other methods embodying the invention could compare any two or more disparate types of data.

A process embodying the invention, such as the one described above in connection with FIG. 11, could be used to rapidly compare perimetry data, or any other type of visual sensitivity or acuity information, to each of a large number of images of a biological structure responsible for vision. The method could be used to automatically identify a defect or condition of a biological structure which gives rise to a loss of vision.

In each of the embodiments described above, two disparate types of data are combined to create a combined presentation. The combined presentation can then be used by medical personnel to facilitate the diagnosis of a defect or condition. In other embodiments of the invention, two disparate types of test data, or two sets of the same type of data can be combined to aid in the treatment of a target tissue.

In a first embodiment of the present invention designed to aid in the treatment of a target tissue, a previously recorded image of the target tissue is combined with a real-time image of the target tissue. For instance, such a device and method can be used to aid in the treatment of leaking blood vessels within a patient's eye.

Several known diseases and eye conditions can cause blood vessels within a patient's eye to leak blood. This condition is typically diagnosed by fluorescent dye angiography. During fluorescent dye angiography, a fluorescent dye is injected into a patient's bloodstream, and the fluorescent dye circulates through the leaking blood vessels within a patient's eye. The eye is then illuminated with wavelengths of light which excite fluorescent emissions from the dye. The fluorescent emissions from the dye can then be used to locate the blood vessels themselves, and areas where the blood vessels are leaking.

Figure 12:
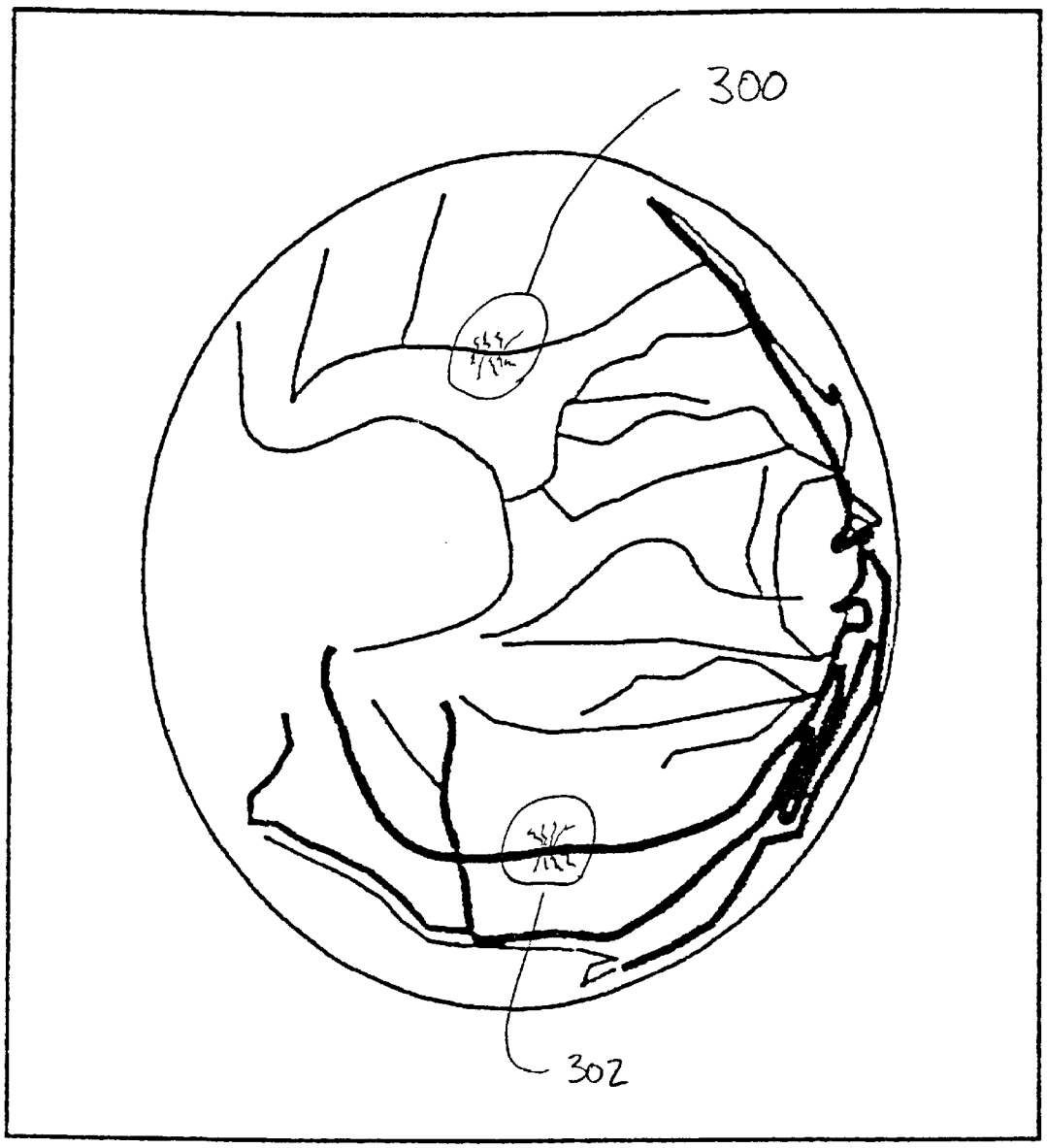
FIG. 12 is a fundus image of an eye.

FIG. 12 is a fundus image taken of a patient's eye during a fluorescent dye angiography procedure. The thicker dark lines appearing in FIG. 12 correspond to the fluorescent emissions detected during the angiography procedure. As can be seen in FIG. 12, two portions of the blood vessels are leaking at the circled areas identified with reference numbers 300 and 302. Once the leaking blood vessels have been identified in a patient's eye, as shown in FIG. 12, a corrective procedure can be conducted to seal the leaking blood vessels.

One common procedure for sealing leaking blood vessels in a patient's eye utilizes a beam of laser light to cauterized or coagulate the leaking portion of the blood vessels. Usually, an surgeon performing such a procedure will utilize a previously recorded image, such as the one shown in FIG. 12, to locate the leaking areas within the patient's eye. The previously recorded fundus image from the fluorescent dye angiography procedure indicates the portions of the blood vessels that must be cauterized or coagulated to correct the leaking condition.

During the procedure, the surgeon will first examine the fundus image and select an area where a blood vessel is leaking. The surgeon will then look through an aiming mechanism on the laser device and focus the device onto the selected portion of the patient's eye. Note, at this point in time, the leaking blood vessel will generally not be visible to the surgeon. The surgeon must rely on the previously recorded fundus image to determine the location where the leak exists. Thus, the surgeon must rely on his own ability to focus the laser device at the appropriate position in the patient's eye. The laser is then activated to seal the leaking blood vessel.

If the procedure is performed properly, the leaking portion of a blood vessel will be cauterized, and the leaking will be sealed. Unfortunately, because the surgeon is not able to directly view the leaking portion of the blood vessel during the cauterization procedure, the surgery is not always successful.

In a device embodying the present invention, a previously recorded fundus image from a fluorescent dye angiography is superimposed onto a real-time image of the patient's eye during the actual laser procedure. The real-time image is captured by the laser device itself. The combined image allows the surgeon to easily focus the laser device onto leaking blood vessels of a patient's eye so that the cauterization procedure will be successful.

Figure 13:
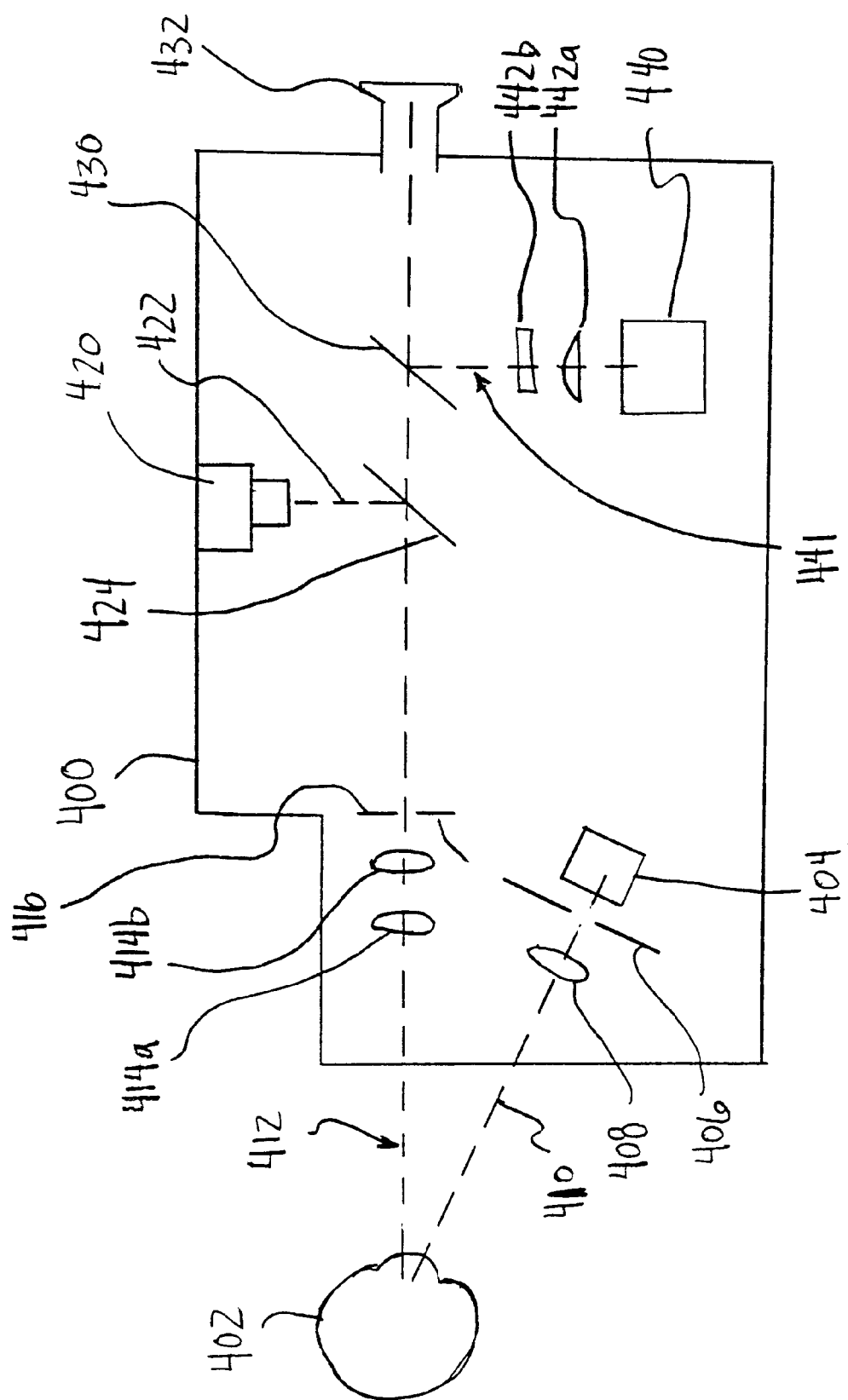
FIG. 13 is a diagram showing elements of another device embodying the invention.

A device embodying the present invention, that allows a surgeon to seal leaking blood vessels in a patient's eye, is shown in FIG. 13. The laser device 400 includes a laser 420, an image generating device 440, and an illumination device 404.

In operation, the illumination device 404 generates a relatively low intensity illumination light which is focused through a slit aperture 406, and a focusing lens 408, along a first axis 410. The slit aperture 406 and the focusing lens 408 are used to selectively focus the illumination light onto selected portions of the patient's eye. The illumination light then impinges on the patient's eye, where it is reflected by the various structures within the patient's eye.

The reflected illumination light then progresses back along a second optical path 412, through one or more focusing elements 414a, 414b, and through a second slit aperture 416. The focusing elements 414a, 414b, and the second slit aperture 416 are designed to focus the laser and a viewing optical onto the same portion of the patient's eye illuminated by the illumination device 404. Thus, the two optical axes of the device 410 and 412 are configured in a confocal arrangement.

The reflected light then passes through a first dichroic reflecting element 424, a second dichroic reflecting element 430, and the reflected illumination light passes through a viewing ocular 432, which the surgeon uses to view the selected portion within the patient's eye 402. This allows the surgeon to view the selected portion of the patient's eye 402 upon which the device is focused.

An image generating device 440 is used to project a previously recorded image of the patient's eye through various focusing elements 442a, 442b. The previously recorded image of the patient's eye is then reflected by the second dichroic reflective element 430 to the ocular 432.

The previously recorded image of the patient's eye will typically be a fundus image taken during a fluorescent dye angiography procedure. The previously recorded image will indicate those portions of the blood vessels within the patient's eye that are leaking blood. The projected image generated by the image generating device 440 will be superimposed onto the image of the eye provided by the reflected light. Thus, a surgeon viewing the eye 402 through the ocular 432 will see both a real-time image of the patient's eye, and a superimposed previously recorded fundus image projected by the projecting device 440.

The projected image from the projecting device 440 will be selectively focused by the focusing elements 442a, 442b so that the previously recorded image will be properly superimposed onto the real-time image visible through the ocular 432. The focusing performed by the focusing elements 442a, 442b may include scaling or inverting the image generated by the image generating device 440 so that the previously recorded image is properly superimposed onto the visible real-time image. In addition, if only a small portion of the patient's eye 402 is visible through the ocular 432, only the corresponding small portion of the previously recorded fundus image should be superimposed onto the real-time image.

Once the surgeon focuses the device onto the proper portion of the patient's eye, the laser 420 would be used to selectively generate a beam of laser light that is projected along a laser projection optical axis 422. The laser beam would be reflected by the first dichroic reflecting element 424, along the second optical path 412, and through the slit aperture 414 and the focusing elements 412a, 412b. The focused laser beam would then be projected onto the selected portion of the patient's eye 402 currently visible through the ocular 432. The laser beam could be used to seal selected blood vessels within the patient's eye to prevent further leakage of blood The embodiment described above, and illustrated in FIG. 13, allows a surgeon to simultaneously view a previously recorded image of a patient's eye, and a real-time image of the patient's eye. This allows the surgeon to focus the laser device onto exactly the right portion of the patient's eye so that a corrective procedure can be successfully performed.

Although the embodiment shown in FIG. 13 uses an ocular 432 to focus the device onto the proper portion of a patient's eye, in alternate embodiments of the invention the ocular 432 could be replaced with a projection screen, or a video monitor. For instance, the ocular 432 could be replaced with one or more charged coupled devices capable of receiving the reflected light from the patient's eye 402 and the previously recorded image generated by the image generating device. The signals from the charge coupled device(s) would then be used to drive a screen, such as a video monitor or projector.

In such an embodiment, a single charge coupled device could be substituted for the ocular shown in FIG. 13, or two different charge coupled devices could be used. If two charge coupled devices were used, one could be used to capture the light reflected from the patient's eye, and another could be used to capture the previously recorded image of the patient's eye generated by the image generating device 440. The signals from both charge coupled devices would then be used to drive a monitor or display.

In still other embodiments, the image generating device could be replaced with a data storage device that is configured to supply data from a previously recorded image. In this instance, a charge coupled device could be substituted for the ocular shown in FIG. 13, and used to capture a real image of the patient's eye. The data from the charge coupled device could then be combined with the previously recorded image data from the storage device, and the combined data could be displayed on a monitor or display screen. In this embodiment, a processor and associated software could combine the previously recorded image data and the real-time image data. The processor and the software could also include the ability to scale or invert either or both of the real-time and previously recorded image data, and the ability to select a small portion of a previously recorded image for superposition onto the real-time image.

A general block diagram of the device as shown in FIG. 13 is also illustrated in FIG. 9. In FIG. 9, the treatment device 1085 would correspond to the laser device 420 show in FIG. 13. The combining device 1040 shown in FIG. 9 would correspond to the illumination device 404, the focusing elements 406, 408, 141a, 414b, 416, the dichroic elements 424, 430, the projection device 440 and its associated focusing elements 442a, 442b, and the ocular 432.

Although the embodiment shown in FIG. 13 is intended to be used to seal selected blood vessels within a patient's eye, the generalized device shown in FIG. 9 could be used to accomplish many other types of treatment procedures. For instance, if the treatment device 1085 is a laser, the laser could be used to selective cauterize blood vessels in any portion of a patient's body. In addition, instead of superimposing a previously recorded fundus image and a real-time image of a patient's eye, the device shown in FIG. 9 could combine any type of previously recorded data with any other real-time data to facilitate the delivery or application of treatment to a target tissue with the treatment device 1085. For instance, the infrared imager 1095, ultrasound imager 1096, or thermal imager 1097 could be used to acquire and record data relating to internal body organs or structures of a patient's body. Such previously recorded data could then be superimposed onto a real-time data to help a medical personnel to selectively aim treatment delivered by a treatment device 1085 to the most appropriate portion of the patient's body.

The treatment device could be a laser, or any other type of device intended to deliver treatment to a patient's body. For instance, the treatment device could also be a drug delivery device, a tissue sampling device, or any other type of device designed to accomplish diagnostic or corrective actions on a patient's body tissues.

Furthermore, although the embodiments described immediately above are intended to superimpose a previously recorded image or set of test data onto real-time images or test data, a device embodying the invention could also be used to superimpose two different disparate types of test data to aid in the treatment of a target tissue. For instance, in some of the embodiments described above, perimetry data and fundus images are combined to create combined presentations. The combined presentations could allow a surgeon to identify selected structures within a patient's eye that are responsible for reduced visual sensitivity, as reflected in the perimetry data. A surgeon could then perform a corrective procedure, with a treatment device, utilizing the combined presentation as a guide to determine where the treatment should be applied. Such a device would also fall within the ambient of the present invention.

Figure 14:
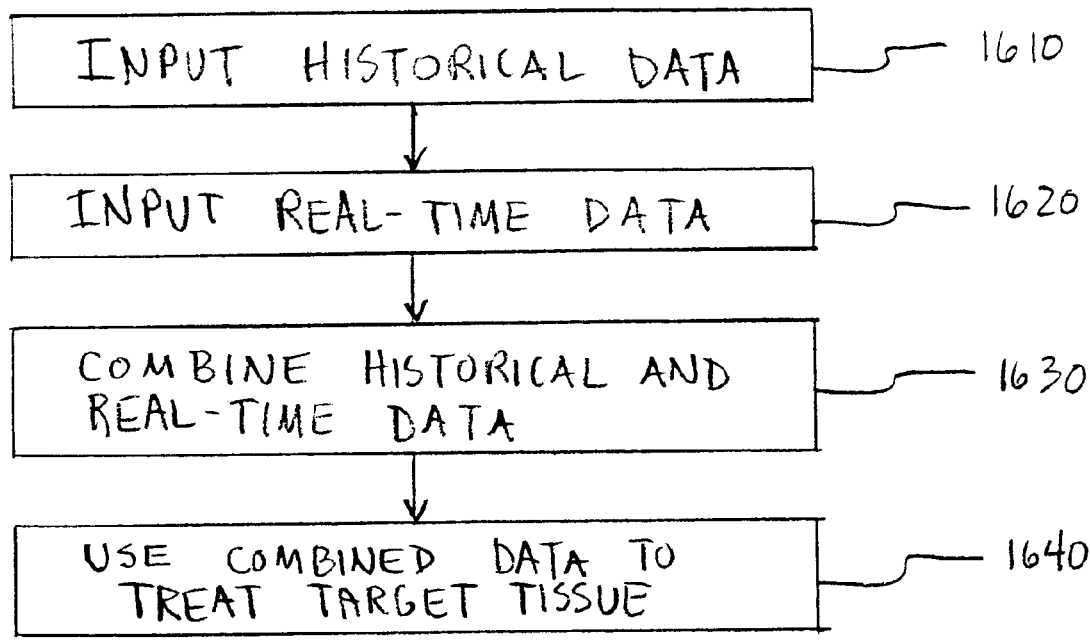
FIG. 14 is a flow chart showing steps of another method embodying the invention.

A first generalized method embodying the present invention is shown in FIG. 14. In this method, in step 1610, historical data is input into a device embodying the invention. The historical data could represent previously recorded data or images relating to a target tissue. Next, in step 1620, real-time data is input to the device. In step 1630, the historical and real-time data is combined. This can involve selecting only a small portion of the historical data for combination with the real-time data. This could also involve the scaling of either the historical data or the real-time data, or inversion of or rotation of the historical and/or real-time data.

In step 1640, the combined data is used to treat a target tissue. As described above, this can involve utilizing the combined data to target a selected portion of a target tissue.

Figure 15:
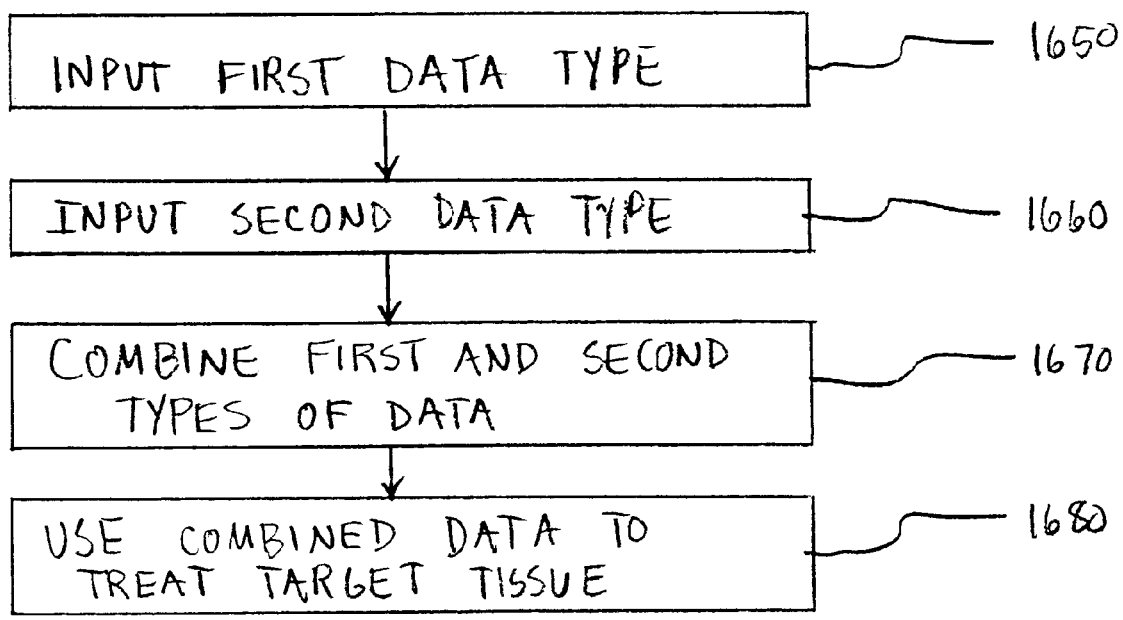
FIG. 15 is a flow chart showing steps of yet another method embodying the invention.

A second method embodying the present invention is shown in FIG. 15. In step 1650, a first type of data is input to a device embodying the invention. In step 1660, a second type of data is input to the device. The first and second types of data can be similar types of data, or disparate types of data.

In step 1670, the first and second types of data are combined to create a combined presentation. This can involve scaling, rotation, inversion, or other manipulation steps that are necessary to combine the first and second types of data to create an intelligible combined presentation. In step 1680, the combined data is then used to treat a target tissue, as described above.

It is to be understood that the foregoing embodiments are merely illustrative. Numerous variations, modifications and changes could be made to the above described embodiments without departing from the scope and spirit of the invention, as defined in the following claims.

What is claimed is:

1. A method of treating a target tissue, comprising:
   combining a first type of biological data and a second type of biological data to generate a combined presentation; and
   using the combined presentation to aid treatment of a target tissue wherein the first type of data and the second type of data are similar types of data and the combining step comprises superimposing the first type of data and the second type of data.

2. The method of claim 1, wherein the first type of data is previously recorded data and wherein the second type of data is real-time data.

3. The method of claim 1, wherein the combining step further comprises scaling one of the first type of data and the second type of data.

4. The method of claim 1, wherein the combining step further comprises rotating one of the first type of data and the second type of data.

5. The method of claim 1, wherein the combining step further comprises inverting one of the first type of data and the second type of data.

6. The method of claim 1, wherein the first and second types of biological data are first and second types of diagnostic data.

7. A method of treating a target tissue, comprising the steps of:
   combining a first type of data and a second type of data to generate a combined presentation; and
   using the combined presentation to aid treatment of a target tissue,
   wherein the first type of data is a previously recorded image of the target tissue, wherein the second type of data is a real-time image of the target tissue, and wherein the combining step comprises superimposing the previously recorded image into the real-time image.

8. The method of claim 7, wherein the combining step further comprises selecting a portion of the previously recorded image for superposition onto the real-time image.

9. The method of claim 7, wherein the using step comprises using the superimposed image to direct a laser beam to a selected portion of the target tissue.

10. A method of treating a target tissue, comprising:
    combining a first type of biological data and a second type of biological data to generate a combined presentation; and
    using the combined presentation to aid treatment of a target tissue, wherein the using step comprises using the combined presentation to direct a laser beam to a selected portion of the target tissue.

11. A method of treating a target tissue, comprising:
    combining a first type of biological data and a second type of biological data to generate a combined presentation; and
    using the combined presentation to aid treatment of a target tissue, wherein the using step comprises using the combined presentation to direct a drug to a selected portion of the target tissue.

12. A method of treating a target tissue, comprising:
    combining a first type of biological data and a second type of biological data to generate a combined presentation; and
    using the combined presentation to aid treatment of a target tissue, wherein the using step comprises using the combined presentation to direct a treatment to a selected portion of the target tissue.

13. A method of treating a target tissue, comprising:
    combining a first type of biological data and a second type of biological data to generate a combined presentation; and
    using the combined presentation to aid treatment of a target tissue, wherein the first type of data is different from the second type of data.

14. The method of claim 13, wherein the using step comprises using the combined presentation to direct a treatment to a selected portion of the target tissue.

15. The method of claim 13, wherein the combining step comprises manipulating at least one of the first and second types of data to create the combined presentation.

16. The method of claim 13, wherein the combining step comprises at least one of scaling, rotating and inverting at least one of the first type of data and the second type of data.

17. The method of claim 13, wherein the first and second types of biological data are first and second types of diagnostic data.

18. A device for treating a target tissue, comprising:
    combining means for combining a first type of biological data and a second type of biological data to generate a combined presentation; and
    means for using the combined presentation to aid treatment of a target tissue, wherein the combining means is configured to perform at least one of a scaling operation, a rotation operation and an inversion operation on at least one of the first type of data and the second type of data to create the combined presentation.

19. The device of claim 18, wherein the combining means is configured to combine similar types of data.

20. The device of claim 18, wherein the first and second types of biological data are first and second types of diagnostic data.

21. A device for treating a target tissue, comprising:
    combining means for combining a first type of biological data and a second type of biological data to generate a combined presentation; and
    means for using the combined presentation to aid treatment of a target tissue, wherein the combining means is configured to superimpose the first type of data onto the second type of data to create the combined presentation.

22. The device of claim 21, wherein the combining means is configured to select a portion of the first type of data for superposition onto the second type of data.

23. The device of claim 21, wherein the combining means is configured to combine similar types of data.

24. The device of claim 21, wherein the first and second types of biological data are first and second types of diagnostic data.

25. A device for treating a target tissue, comprising:

combining means for combining a first type of biological data and a second type of biological data to generate a combined presentation; and means for using the combined presentation to aid treatment of a target tissue, wherein the means for using comprises a device for viewing the combined presentation to aid the treatment of the target tissue.

26. The device of claim 25, wherein the device for viewing the combined presentation aids the aiming of a treatment laser beam to a selected portion of the target tissue.

27. A medical device for aiding the treatment of a target tissue, comprising:

a combining device configured to combine a first type of biological data and a second type of biological data to generate a combined presentation wherein the combining device is configured to perform at least one of a scaling operation, a rotation operation and an inversion operation on at least one of the first type of data and the second type of data to generate the combined presentation; and a presentation device configured to present the combined presentation in a manner that aids treatment of a target tissue.

28. The medical device of claim 27, wherein the first and second types of biological data are first and second types of diagnostic data.

29. A medical device for aiding the treatment of a target tissue, comprising:

a combining device configured to combine a first type of biological data and a second type of biological data to generate a combined presentation, wherein the combining device is configured to superimpose the first type of data onto the second type of data to generate the combined presentation; and a presentation device configured to present the combined presentation in a manner that aids treatment of a target tissue.

30. The device of claim 29, wherein the combining device is configured to select a portion of the first type of data for superposition onto the second type of data.

31. The medical device of claim 29, wherein the first and second types of biological data are first and second types of diagnostic data.

32. A medical device for aiding the treatment of a target tissue, comprising:

a combining device configured to combine a first type of biological data and a second type of biological data to generate a combined presentation; and a presentation device configured to present the combined presentation in a manner that aids treatment of a target tissue, wherein the presentation device is configured to display the combined presentation in such a manner that it can be used to direct a treatment to a selected portion of the target tissue.

33. A medical device for aiding the treatment of a target tissue, comprising:

a combining device configured to combine a first type of biological data and a second type of biological data to generate a combined presentation;

an input device for inputting at least one of the first type of data and the second type of data; and a presentation device configured to present the combined presentation in a manner that aids treatment of a target tissue.

34. A medical device for aiding the treatment of a target tissue, comprising:

a combining device configured to combine a first type of biological data and a second type of biological data to generate a combined presentation;

a device for generating at least one of the first type of data and the second type of data; and a presentation device configured to present the combined presentation in a manner that aids treatment of a target tissue.

35. A medical device for aiding the treatment of a target tissue, comprising:

a combining device configured to combine a first type of data and a second type of data to generate a combined presentation; and a presentation device configured to present the combined presentation in a manner that aids treatment of a target tissue, wherein the first type of data comprises a previously recorded image of the target tissue, wherein the second type of data comprises a real-time image of the target tissue, and wherein the combining device is configured to superimpose the previously recorded image onto the real-time image to create a combined image.

36. A medical device for treating a target tissue, comprising:

a combining device configured to combine a first type of biological data and a second type of biological data to generate a combined presentation;

a treatment device for applying a treatment to a target tissue; and a presentation device configured to present the combined presentation in a manner that aids treatment of the target tissue with the treatment device.

37. The medical device of claim 36, wherein the presentation device is configured to present the combined presentation so that it aids in directing the treatment from the treatment device to a selected portion of the target tissue.

38. The medical device of claim 37, wherein the first type of data comprises first image data, wherein the second type of data comprises second image data, and wherein the combining device is configured to combine the first image data and the second image data to generate a combined image.

39. The medical device of claim 38, wherein the treatment device comprises a laser, and wherein the presentation device presents the combined image such that it aids in aiming the laser at a selected portion of the target tissue.

40. The medical device of claim 39, wherein the first image data comprises previously recorded image data, and wherein the second image data comprises real-time image data.

41. The medical device of claim 40, further comprising an optical device for obtaining the real-time image data.

42. The medical device of claim 41, wherein the optical device comprises a charge coupled device for obtaining real-time image data from the target tissue.

43. The medical device of claim 36, wherein the first type of data and the second type of data are disparate types of data, and wherein the presentation device is configured to present the combined presentation to aid in applying treatment from the treatment device to a selected portion of the target tissue.

44. The medical device of claim 36, wherein the first and second types of biological data are first and second types of diagnostic data.

45. A method of treating a target tissue, comprising:
combining a first type of biological data and a second type of biological data to generate a combined presentation; and
using the combined presentation to aid treatment of a target tissue, wherein the first type of data and the second type of data are similar types of data, wherein the first type of data is a previously recorded image of the target tissue, wherein the second type of data is a real-time image of the target tissue, and wherein the combining step comprises superimposing the previously recorded image into the real-time image.

46. A medical device for aiding the treatment of a target tissue, comprising:
a combining device configured to combine a first type of biological data and a second type of biological data to generate a combined presentation; and
a presentation device configured to present the combined presentation in a manner that aids treatment of a target tissue, wherein the first type of data comprises a previously recorded image of the target tissue, wherein the second type of data comprises a real-time image of the target tissue, and wherein the combining device is configured to superimpose the previously recorded image onto the real-time image to create a combined image.

* * * * *